US012122739B2

(12) United States Patent
Brazdil et al.

(10) Patent No.: US 12,122,739 B2
(45) Date of Patent: Oct. 22, 2024

(54) PROCESS FOR MAKING BIOBASED PRODUCTS FROM SUGARS

(71) Applicant: Archer Daniels Midland Company, Decatur, IL (US)

(72) Inventors: James Brazdil, Glen Ellyn, IL (US); Chi-Cheng Ma, Champaign, IL (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 783 days.

(21) Appl. No.: 17/265,004

(22) PCT Filed: Jul. 31, 2019

(86) PCT No.: PCT/US2019/044400
§ 371 (c)(1),
(2) Date: Feb. 1, 2021

(87) PCT Pub. No.: WO2020/028521
PCT Pub. Date: Feb. 6, 2020

(65) Prior Publication Data
US 2022/0363628 A1   Nov. 17, 2022

(51) Int. Cl.
| | |
|---|---|
| C07C 303/32 | (2006.01) |
| B01J 21/06 | (2006.01) |
| B01J 21/18 | (2006.01) |
| B01J 23/42 | (2006.01) |
| B01J 23/44 | (2006.01) |
| B01J 23/644 | (2006.01) |
| B01J 23/755 | (2006.01) |
| B01J 25/02 | (2006.01) |
| B01J 29/70 | (2006.01) |
| B01J 31/02 | (2006.01) |
| B01J 31/28 | (2006.01) |
| B01J 41/07 | (2017.01) |
| B01J 41/14 | (2006.01) |
| C07C 213/02 | (2006.01) |

(52) U.S. Cl.
CPC .......... *C07C 303/32* (2013.01); *B01J 21/066* (2013.01); *B01J 21/18* (2013.01); *B01J 23/42* (2013.01); *B01J 23/44* (2013.01); *B01J 23/6447* (2013.01); *B01J 23/755* (2013.01); *B01J 25/02* (2013.01); *B01J 29/7007* (2013.01); *B01J 31/0232* (2013.01); *B01J 31/28* (2013.01); *B01J 41/07* (2017.01); *B01J 41/14* (2013.01); *C07C 213/02* (2013.01)

(58) Field of Classification Search
CPC . B01J 21/066; B01J 21/18; B01J 23/42; B01J 23/44; B01J 23/6447; B01J 23/755; B01J 25/02; B01J 29/7007; B01J 31/0232; B01J 31/28; B01J 37/04; B01J 37/082; B01J 41/07; B01J 41/14; C07C 213/02; C07C 215/08; C07C 303/02; C07C 303/24; C07C 303/32; C07C 305/06; C07C 309/14; C07C 45/51; C07C 45/673; C07C 45/79; C07C 45/85; C07C 47/04; C07C 47/19; Y02P 20/582
See application file for complete search history.

(56) References Cited

U.S. PATENT DOCUMENTS

| | | | |
|---|---|---|---|
| 5,331,101 A | 7/1994 | Habermann | |
| 2012/0271068 A1* | 10/2012 | Magerlein | C07C 215/08 564/473 |
| 2015/0183731 A1* | 7/2015 | Hu | C07C 303/02 558/23 |
| 2016/0002137 A1* | 1/2016 | Taarning | A23L 5/41 426/268 |
| 2016/0340301 A1 | 11/2016 | Hu | |

FOREIGN PATENT DOCUMENTS

WO   WO/2020/028521   2/2020

OTHER PUBLICATIONS

International Preliminary Report on Patentability issued on Nov. 15, 2019 for International Application No. PCT/US2019/044400 for Applicant Archer Daniels Midland Company.

* cited by examiner

*Primary Examiner* — Jafar F Parsa
*Assistant Examiner* — Blaine G Doletski
(74) *Attorney, Agent, or Firm* — Andrew F. Nilles

(57) ABSTRACT

An integrated, co-product capable process is provided for producing taurine in particular with optionally one or both of monoethanolamine and diethanolamine from one or more sugars, comprising pyrolyzing one or more sugars to produce a crude pyrolysis product mixture including glycolaldehyde and formaldehyde; optionally removing formaldehyde from the crude pyrolysis product mixture, then combining the crude pyrolysis product mixture with an aminating agent in the presence of hydrogen and further in the presence of a catalyst to produce at least monoethanolamine from the crude pyrolysis product mixture; optionally recovering diethanolamine from the crude reductive amination product, sulfating at least a portion to all of the monoethanolamine product to produce 2-aminoethyl hydrogen sulfate ester; and sulfonating the 2-aminoethyl hydrogen sulfate ester to produce taurine.

14 Claims, 4 Drawing Sheets

PROCESS FOR MAKING BIOBASED PRODUCTS FROM SUGARS

CROSS-REFERENCE TO RELATED APPLICATIONS

This application is a national stage entry of International Application No. PCT/US19/44400, filed Jul. 31, 2019, which itself claims priority to U.S. Provisional Patent Application Nos. 62/713,777, filed Aug. 2, 2018, 62/713,787, filed Aug. 2, 2018, and 62/769,035, filed Nov. 18, 2018, the contents of each are incorporated herein by reference.

TECHNICAL FIELD

The present invention relates to processes for making ethanolamine products, and also to processes for making the aminosulfonic acid nutritional supplement taurine (2-aminoethanesulfonic acid).

BACKGROUND ART

Monoethanolamine (MEA) is an industrial commodity that is presently produced by treating ethylene oxide with aqueous ammonia, a process that also produces diethanolamine (DEA) and triethanolamine (TEA) through the reaction of MEA and DEA, respectively, with additional equivalents of ethylene oxide. MEA is used as a feedstock for producing detergents, emulsifiers, polishes, pharmaceuticals, corrosion inhibitors and chemical intermediates, and finds widespread usage in amine gas treating of flue gas and sour natural gas to remove carbon dioxide and hydrogen sulfide. DEA finds use in the same amine gas treating applications and as a surfactant and corrosion inhibitor, while TEA is used in a variety of cosmetics and personal care products.

The sourcing of these important commodity products from ethylene oxide, however, is problematic in that ethylene oxide is extremely flammable, and its mixtures with air are explosive and have been the cause of a number of industrial accidents over the years.

Taurine, or 2-aminoethanesulfonic acid, is a conditional amino acid that is naturally produced by the human body and that has become increasingly popular as a nutritional supplement for humans, with reputed benefits for reducing cardiovascular disease and helping in the treatment of congestive heart failure, decreasing the side effects from Parkinson's disease, reducing metabolic syndrome, as an antioxidant in aiding patients with periodontal disease and improving athletic performance. Taurine is also widely used in animal nutritional products, in fact, being required in dry and wet cat foods in the United States to combat central retinal degeneration and feline dilated cardiomyopathy.

Methods for making synthetic taurine commercially have included a method wherein ethylene oxide is reacted with sodium bisulfite to obtain sodium isethionate, which then undergoes ammonolysis to yield sodium taurinate. Neutralization with sulfuric acid results in a mixture of taurine and sodium sulfate. This method obviously has the same drawback of a dependence on ethylene oxide with its attendant hazards. In another known method, monoethanolamine can be reacted with sulfuric acid to yield 2-aminoethyl hydrogen sulfate ester (AES), and subsequently reacting the AES with sodium sulfite yields again taurine and sodium sulfate. A variation of the first, ethylene oxide process described in U.S. Pat. No. 8,609,890 reacts the sodium taurinate with sulfur dioxide or sulfurous acid to yield taurine and regenerate sodium bisulfite which can be recycled and reused, rather than generating sodium sulfate.

While the commodity chemical monoethanolamine has thus been known as a material from which the specialty material taurine could be synthesized, and while methods have been described for producing ethanolamines from renewable resources such as sugars, see, e.g., U.S. Pat. No. 9,796,649 to Taarning et al., nevertheless an integrated process with the capability of efficiently producing one or more ethanolamines and taurine as co-products from renewable resources, as desired, has not been described in the literature and would be commercially attractive.

SUMMARY OF THE INVENTION

The following presents a simplified summary of the invention in order to provide a basic understanding of some of its aspects. This summary is not an extensive overview of the invention, thus the mention or omission of a particular feature should not be understood as implying, respectively, that the feature is indispensable or of lesser significance. The sole purpose of this summary is to present some concepts of the invention in a simplified form as a prelude to the more detailed description that is presented later.

With this understanding, the integrated, co-product capable process of the present invention from one perspective may be seen as providing a novel process for producing taurine in particular, comprising pyrolyzing a sugar or a mixture of sugars, such as an aqueous solution of glucose, fructose or sucrose, to produce a crude pyrolysis product mixture including glycolaldehyde and formaldehyde; combining the crude pyrolysis product mixture (without undertaking to first remove any of the formaldehyde therefrom) with an aminating agent in the presence of hydrogen and further in the presence of a catalytic combination including at least a nickel catalyst and an acidic co-catalyst component, in which the nickel catalyst is from 1 to 99 percent by weight of the total weight of the combination and the acidic co-catalyst forms the remainder, to produce a monoethanolamine product from the crude pyrolysis product mixture; sulfating the monoethanolamine product to produce 2-aminoethyl hydrogen sulfate ester; and sulfonating the 2-aminoethyl hydrogen sulfate ester to produce taurine.

In this regard, the above-referenced U.S. Pat. No. 9,796,649 to Taarning et al. (Taarning) describes processes for using compositions from the pyrolysis of sugars, comprising low molecular weight carbonyl compounds primarily in the form of glycolaldehyde (or hydroxyacetaldehyde) but also including formaldehyde, glyoxal and pyruvaldehyde, for a variety of subsequent chemical transformations including the synthesis of ethylene and propylene glycol through hydrogenation, the synthesis of flexible phenolic carbamido resins, making straight and branched chain oxygenated $C_4$-alkyl and $C_4$-alkenyl compounds and amines such as ethanolamine (MEA), ethylenediamine and dimethylethanolamine.

Taarning indicate, however, that formaldehyde is a well-known poison for those subsequent chemical transformations—such as the reductive amination methods by which such amine products may be made—and propose converting formaldehyde in the crude pyrolysis product to formaldehyde acetals and removing the same from the crude pyrolysis product to a sufficient extent that the remaining pyrolysis product can be used in the reductive amination, by reactive distillation in the presence of at least one alcohol and a catalyst.

Thus, from another perspective, a process is provided by the present invention for making taurine, in particular, that involves carrying out a reductive amination on the crude product from the pyrolysis of sugars such as dextrose according to, for example, a process as described in U.S. Pat. No. 7,094,932 to Majerski et al. or as described in any of the other representative references described hereafter as relating to methods for the pyrolysis of sugars, comprising glycolaldehyde, formaldehyde, glyoxal and pyruvaldehyde, without however necessitating the use of an impractical reactive distillation to greatly reduce the amount of formaldehyde in the reductive amination feed.

In other embodiments, the integrated, co-product capable process of the present invention provides alternative methods for producing taurine, in particular, wherein formaldehyde in the crude product from the pyrolysis of dextrose is reduced by either carrying out an oxidation in the presence of a catalyst and/or by bringing the crude product in contact with a formaldehyde-scrubbing material that retains formaldehyde from the crude product but leaves glycolaldehyde in the crude product for carrying out a reductive amination thereon to form monoethanolamine, which is then sulfated to provide 2-aminoethyl hydrogen sulfate ester, which in turn is sulfonated to provide taurine.

From another perspective, a process is provided for producing both of taurine and monoethanolamine as co-products, by using but a portion of the monoethanolamine as a feed for the synthesis of the taurine—with either carrying out the reductive amination with or without formaldehyde removal beforehand (where "formaldehyde removal" is understood both here and hereafter as encompassing the use of a catalytic oxidation step on at least the formaldehyde in the crude pyrolysis product as well as formaldehyde's retention on a formaldehyde-scrubbing material brought into contact with the crude pyrolysis product), in the latter scenario, for example, using a catalytic combination including a nickel catalyst component and an acidic co-catalyst component, wherein the nickel catalyst component is from 1 to 99 percent by weight of the total weight of the combination and the acidic co-catalyst forms the remainder of the combination. In certain embodiments, a hydrogenation catalyst and acid co-catalyst as described in greater detail hereafter are deployed for improved selectivity to the monoethanolamine.

From yet another perspective, a process is provided for producing taurine, monoethanolamine and diethanolamine as co-products, by separating out and recovering a diethanolamine product from a reductive amination step providing both of monoethanolamine and diethanolamine—with again either carrying out the reductive amination with or without a preceding formaldehyde removal step—and then again using but a portion of the monoethanolamine for the synthesis of the taurine. In certain embodiments wherein relatively more diethanolamine is desired, instead of a catalytic combination including from 1 to 99 percent by weight of a nickel catalyst component with the remainder of an acidic co-catalyst component, or a hydrogenation catalyst and acid co-catalyst per the above-referenced MEA-directed embodiments, a catalyst including at least one noble metal is used as described in greater detail hereafter.

Figure 1:
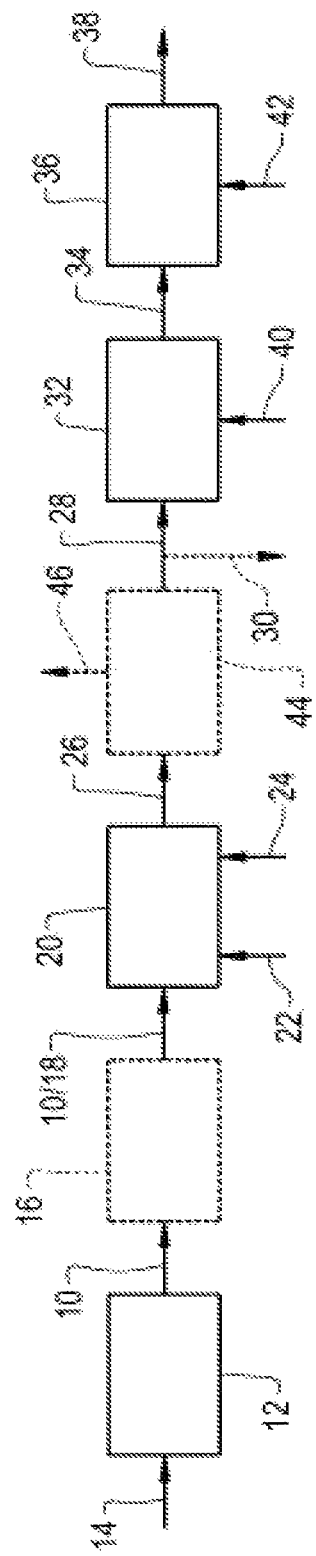
FIG. 1 is a schematic drawing of an embodiment of a process of the present invention.

The Figures are to be understood to present certain embodiments of the invention to aid in understanding of the principles and reaction chemistry involved, but not to limit the scope of the invention as defined in the appended claims. As would be apparent to one of skill in the art, with the knowledge gained from the present disclosure, reductive amination processes according to various other embodiments of the invention will utilize particular catalysts, co-catalysts, and reaction conditions determined, at least in part, according to specific objectives.

DETAILED DESCRIPTION OF EMBODIMENTS

As used in this application, the singular forms "a", "an" and "the" include plural references unless the context clearly indicates otherwise. The term "comprising" and its derivatives, as used herein, are similarly intended to be open ended terms that specify the presence of the stated features, elements, components, groups, integers, and/or steps, but do not exclude the presence of other unstated features, elements, components, groups, integers and/or steps. This understanding also applies to words having similar meanings, such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers, and/or steps. The term "consisting essentially of", as used herein, is intended to specify the presence of the stated features, elements, components, groups, integers, and/or steps, as well as those that do not materially affect the basic and novel characteristic(s) of stated features, elements, components, groups, integers, and/or steps.

Where specific numerical values are used to quantify certain parameters relating to the invention, and where the specific numerical values are not expressly part of a numerical range, it will be understood that each such specific numerical value provided herein is to be construed as providing literal support for a broad, intermediate and narrow range of values for the parameter in question. The broad range shall be the numerical value plus and minus 60 percent of the numerical value, rounded to two significant digits. The intermediate range shall be the numerical value plus and minus 30 percent of the numerical value, rounded to two significant digits, while the narrow range shall be the numerical value plus and minus 15 percent of the numerical value again to two significant digits. Further, these broad, intermediate and narrow numerical ranges should be applied not only to the specific values, but also to the differences between these specific values. Thus, if the specification describes a first pressure of 110 kPa for a first stream and a second pressure of 48 kPa (a difference of 62 kPa) for a second stream, the broad, intermediate and narrow ranges for the pressure difference between these two streams would be 25 to 99 kPa, 43 to 81 kPa, and 53 to 71 kPa, respectively.

Where the present description uses numerical ranges to quantify certain parameters relating to the invention, it will be similarly understood that these ranges are to be construed as providing literal support for claim limitations that only recite the lower value of the range as well as claim limitations that only recite the upper value of the range.

Unless otherwise indicated, any definitions or embodiments described in this or in other sections are intended to be applicable to all embodiments and aspects of the subjects herein described for which they would be suitable according to the understanding of a person of ordinary skill in the art.

As indicated above, the present invention concerns a process capable of the efficient production of taurine with optional co-products in the form of monoethanolamine and diethanolamine, as contemplated in a variety of related embodiments.

Turning now to FIG. 1, a schematic illustration is provided of such a process. Initially, a composition 10 comprising low molecular weight carbonyl compounds, and specifically including glycolaldehyde and some amount of formaldehyde, is obtained in certain embodiments by the pyrolysis in step 12 of organic matter 14 such as biomass, wood or sugars in a known manner. The pyrolysis or hydrous thermolysis of sugars to provide a product mixture comprising glycolaldehyde and various other oxygen-containing compounds is described in various publications, including, for example, WO 2018/104508 A1 to Osmundsen et al.; WO 2017/216311 A1 to Larsen et al; U.S. Pat. No. 7,094,932 to Majerski et al. and U.S. Pat. No. 10,077,222 to Holm et al. (citing use of a process according to U.S. Pat. No. 7,094,932 in the context of producing ethylene glycol from glycolaldehyde); U.S. Pat. Nos. 5,252,188 and 5,393,542 to Stradal et al.; U.S. Pat. No. 5,292,541 to Underwood et al.; U.S. Pat. No. 5,397,582 to Underwood et al.; and Tomasik et al., "The Thermal Decomposition of Carbohydrates, Part I. The Decomposition of Mono-, Di-, and Oligo-Saccharides", Advances in Carbohydrate Chemistry and Biochemistry, vol. 47, pp. 203-278 (1989) and the references cited in any of these as describing processes for the pyrolysis of sugars, especially, of an aqueous sugar solution such as an aqueous dextrose solution.

While many methods are thus known for the pyrolysis or hydrous thermolysis of sugars to provide a product mixture comprising glycolaldehyde and various other oxygen-containing compounds and could be used for generating a composition 10 in the context of the present invention, preferred methods will produce comparatively greater amounts of glycolaldehyde and acetol and lesser amounts of other components such as glyoxal, pyruvaldehyde and formaldehyde, with formaldehyde in particular appearing to be undesirable.

In U.S. Pat. No. 7,094,932 to Majerski et al. as specifically referenced in U.S. Pat. No. 9,796,649 to Taarning et al., for example, aqueous sugar solutions containing from 25 to 80 percent of water (serving as the organic matter stream 14 in FIG. 1) are sprayed in a step 12 as a fine mist of 200 microns diameter or less and preferably of 50 microns or less into a reactor held at between 500 and 600 degrees Celsius, and over the course of a residence time of from 0.1 to 5 seconds, produce a vaporous product that is then condensed to provide a composition that is described in Majerski et al. as containing glycolaldehyde with "high specificity" as well as "some" formaldehyde. Preferred sugars are said to be the aldose monomeric sugars, for example, fructose, sucrose and/or especially dextrose (glucose), and yields of glycolaldehyde in the condensed liquid (used in certain embodiments directly as composition 10) are reported to be a minimum of 30 percent by weight based on the weight of sugar(s) in the aqueous solution.

After the pyrolysis of sugars according to Majerski et al. or any other method in which formaldehyde is among the species that are generated in the crude composition 10, in certain embodiments, the composition 10 then undergoes a formaldehyde removal step 16 to provide a reduced formaldehyde pyrolysis product mixture 18. A reduced formaldehyde pyrolysis product mixture 18 will have at least a reduced level of formaldehyde compared to the composition 10, but preferably will comprise less than 1.5 percent by weight of formaldehyde, still more preferably less than 1.0 percent by weight of formaldehyde, still more preferably less than 0.5 percent by weight, still more preferably less than 0.1 percent by weight and even more preferably less than 0.05 percent by weight of formaldehyde, down to a formaldehyde content that is below detection limits.

In certain embodiments, the formaldehyde removal step 16 may involve a selective catalytic oxidation such as, but not being limited to, a type currently known for the removal of formaldehyde from ambient environments, for example, a room temperature oxidation in ambient air with a platinum and bismuth on carbon catalyst as exemplified in Example 2 below. In other embodiments, the formaldehyde removal step 16 may involve scrubbing formaldehyde from a composition 10 by exposure to a suitable adsorbent, for example, a resin such as the Purolite™ A110 macroporous polystyrenic weak base anion exchange resin with primary amine functionality found effective in Example 6 below, or greensand as found suitable in Example 7.

The reduced formaldehyde pyrolysis product mixture 18 then undergoes a reductive amination step 20 in which the mixture 18 is combined with an aminating agent 22 and a source of hydrogen 24 in the presence of a catalyst to form a reductive amination product mixture 26 from glycolaldehyde in the mixture 18.

The catalyst used in the reductive amination step 20 is in certain embodiments preferably selected according to the amine products or combination of amine products that are ultimately desired to be produced by the overall co-product capable process from among monoethanolamine, diethanolamine and taurine, in particular.

Thus, in embodiments wherein taurine is principally desired or wherein monoethanolamine and taurine are desired in preference to diethanolamine, a catalyst and reductive amination process are preferred for the step 20 following the (optional) formaldehyde removal step 16, in which the desired reductive amination reaction pathway can be depicted as:

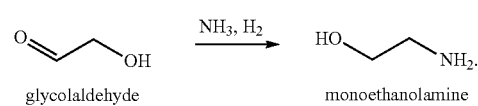

Parenthetically, the term "glycolaldehyde" as used in the referenced application and as used herein is meant to encompass the compound shown above, as well as various forms that this reactive compound may undertake, such as in an aqueous environment of a reaction mixture as described herein. Such forms include glycolaldehyde dimer and oligomer forms, as well as hydrated forms. Glycolaldehyde dimer is a particularly prevalent form, and this form is also known as the ringed structure, 2,5-dihydroxy-1,4-dioxane. For purposes of determining molar selectivity to, and theoretical yield of, monoethanolamine, each mole of glycolaldehyde dimer is considered equivalent to two moles of glycolaldehyde. Similar considerations apply to other glycolaldehyde oligomers.

"Molar selectivity to monoethanolamine" is the percentage, on a molar basis, of converted glycolaldehyde, which results in the formation of monoethanolamine. The yield of monoethanolamine is the amount obtained, expressed as a percentage of the theoretical amount that would be obtained by reacting glycolaldehyde with 100% conversion and 100% molar selectivity to monoethanolamine. The yield can be determined as the product of conversion and selectivity. Therefore, if 10 moles of glycolaldehyde are reacted, 1 mole of glycolaldehyde remains (unreacted) in the product mixture, and 7 moles of monoethanolamine are present in this mixture, then (i) the conversion of glycolaldehyde is 90% (or 90 mole-%), (ii) the molar selectivity to monoethanolamine is 78%, (the formation of 7 moles of monoethanolamine resulting from the conversion 9 moles of glycolaldehyde), and (iii) the yield of monoethanolamine is 70%. Similar definitions of molar selectivity and yield apply to other reaction products.

Particular embodiments according to the MEA-favoring processes comprise reacting glycolaldehyde (including forms of this compound as described above) with an aminating agent 22 and a source of hydrogen 24 in the presence of both a hydrogenation catalyst and an acid co-catalyst under reductive amination conditions, to produce the monoethanolamine (e.g., in a product mixture 26 from which the monoethanolamine may be recovered, such as in a purified form following one or more separation steps). A representative hydrogenation catalyst is a sponge metal catalyst, referring to a metal or metal alloy in granular or powder form. A preferred hydrogenation catalyst is a sponge nickel catalyst, with the material known as Raney nickel being exemplary. This catalyst is namely a fine-grained solid composed mostly of nickel that is present as a nickel-aluminum alloy. Hydrogenation catalysts may, more generally, include one or more hydrogenation-active metals, such as one or more transition metals selected from the group consisting of nickel (Ni), cobalt (Co), iron (Fe), and ruthenium (Ru). For example, representative hydrogenation catalysts may comprise at least 5% by weight (wt-%), typically at least 10 wt-%, and often at least 15 wt-%, of such metal(s). Such transition metal(s) may be disposed or deposited on a solid support, which is intended to encompass catalysts in which the active metal(s) is/are on the support surface and/or within a porous internal structure of the support. Therefore, in addition to such hydrogenation-active metal(s), representative hydrogenation catalysts may further comprise a solid support, with exemplary solid supports comprising one or more metal oxides, such as those selected from the group consisting of aluminum oxide, silicon oxide, titanium oxide, zirconium oxide, magnesium oxide, strontium oxide, tin oxide, etc. The solid support may comprise all, or substantially all of the one or more of such metal oxides, for example such that the one or more metal oxides are present in an amount, or combined amount, of at least 95% by weight of the solid support.

Advantages are seen in the context of the production of MEA (and by extension for the production of taurine) when a hydrogenation catalyst (e.g., Raney nickel or others described above) is promoted with a co-catalyst having acidity, such as having acid sites in the case of a solid co-catalyst. The co-catalyst may, in particular, be a Lewis acid or have Lewis acid sites in the case of a solid co-catalyst. The density of Lewis acid sites may be measured according to known analytical methods, for example using pyridine-adsorbed Fourier transform infrared (FTIR) spectroscopy, on the basis of integral absorbance of the characteristic band at 1450 cm$^{-1}$. This is described, for example, by Takagaki et al., THE ROYAL SOCIETY OF CHEMISTRY (RSC) ADVANCES (2014), Vol. 4: 43785-91. Representative, solid acid co-catalysts, including those which are solid under the reductive amination conditions (and therefore in the presence of the reaction mixture) have a density of Lewis acid sites of from 50 to 2000 micromoles per gram (μmol/g), typically from 200 μmol/g to 1200 μmol/g, and often from 300 to 900 μmol/g. Unless otherwise noted, the term "acid" or "acidic," when used in reference to a solid co-catalyst, refers to its property of having acid sites, or ability to be titrated with a base (e.g., NaOH) in its "as prepared" form, for example outside of, or prior to, introduction into the reaction mixture used for reductive amination. This also applies with respect to references to particular ranges of acid site density. Without being bound by theory, it is believed that a certain level of acidity, which does not exceed a threshold level, is beneficial for enhancing selectivity to monoethanolamine in reactions described herein. With the knowledge gained from the present disclosure, those skilled in the art can optimize the level of acidity for a given set of reductive amination conditions.

Representative solid acid co-catalysts may comprise zeolitic or non-zeolitic molecular sieves, metal oxides, activated carbon, or resins. In the case of zeolitic molecular sieves, acidity is a function of the silica to alumina ($SiO_2$/$Al_2O_3$) molar framework ratio, with lower ratios corresponding to higher densities of acid sites. In embodiments in which the acid catalyst comprises a zeolitic molecular sieve (zeolite), its silica to alumina molar framework ratio may be less than 200 (e.g., from 5 to 200), or less than 100 (e.g., from 10 to 100). Particular solid acid catalysts may comprise one or more zeolitic molecular sieves (zeolites) having a structure type selected from the group consisting of FAU, FER, MEL, MTW, MWW, MOR, BEA, LTL, MFI, LTA, EMT, ERI, MAZ, MEI, and TON, and preferably selected from one or more of FAU, FER, MWW, MOR, BEA, LTL, and MFI. The structures of zeolites having these and other structure types are described, and further references are provided, in Meier, W. M, et al., Atlas of Zeolite Structure Types, 4th Ed., Elsevier: Boston (1996). Specific examples include zeolite Y (FAU structure), zeolite X (FAU structure), MCM-22 (MWW structure), ZSM-5 (MFI structure), and zeolite beta (BEA structure). Preferred are the structure types BEA and MFI.

Non-zeolitic molecular sieves include ELAPO molecular sieves are embraced by an empirical chemical composition, on an anhydrous basis, expressed by the formula:

$(EL_xAl_yP_z)O_2$, in which EL is an element selected from the group consisting of silicon, magnesium, zinc, iron, cobalt, nickel, manganese, chromium and mixtures thereof, x is the mole fraction of EL and is often at least 0.005, y is the mole fraction of aluminum and is at least 0.01, z is the mole fraction of phosphorous and is at least 0.01 and x+y+z=1. When EL is a mixture of metals, x represents the total amount of the element mixture present. Preparations of various ELAPO molecular sieves are well known in the art and may be found in U.S. Pat. No. 5,191,141 (ELAPO); U.S. Pat. No. 4,554,143 (FeAPO); U.S. Pat. No. 4,440,871

(SAPO); U.S. Pat. No. 4,853,197 (MAPO, MnAPO, ZnAPO, CoAPO); U.S. Pat. No. 4,793,984 (CAPO); U.S. Pat. Nos. 4,752,651 and 4,310,440. Representative ELAPO molecular sieves include ALPO and SAPO molecular sieves.

Other solid acid co-catalysts comprise carbon black or activated carbon, which may optionally be acidified to introduce a desired density of acid functional groups (e.g., by treatment with an appropriate functional group-bearing agent such as nitric acid, acetate, sulfonic acid, etc.). As such, these co-catalysts may generally be referred to acidic carbon or acidic activated carbon. The term "activated carbon" itself refers to a form of carbon that has been treated according to known techniques (e.g., steaming) to increase its surface area and pore volume. Similarly, such co-catalysts may comprise resins, such as ion-exchange resins that have acid functional groups. For example, resins within the group of Amberlyst™ Polymeric Catalysts have sulfonic functional groups. Other resins include those within the Dowex® group. The acidity of any of the types of solid acid co-catalysts described herein may be regulated or attenuated, if necessary, by treatment with a base such as ammonia or pyridine. For example, the zeolite ZSM-5 may be at least partially converted to its ammonium form by contacting with $NH_3$, thereby reducing the acidity, relative to the hydrogen form ZSM-5, to a desired level for a given reductive amination reaction. In general, therefore, ammonium form or ammonium-exchanged zeolites (e.g., $NH_4$—ZSM-5 or $NH_4$—BEA) may be used as acid co-catalysts, particularly those in which ammonia adsorption to provide these forms attenuates Lewis acid strength, such that the Lewis acid site density is adjusted or reduced to a value within the ranges given above. Alternatively, this regulation or attenuation of acidity may occur in situ in the reaction mixture, and particularly in the presence of the aminating agent such as ammonium hydroxide. Yet other solid acid co-catalysts may comprise a metal oxide, such as any one or more of silica, alumina, titania, zirconia, magnesium oxide, calcium oxide, strontium oxide, tin oxide, etc. In the case of tin oxide, it may be present in hydrated and/or acidic forms, for example as metastannic acid or stannous acid.

Metal oxides are also described as useful solid supports for hydrogenation-active metals. Accordingly, it can be appreciated, more generally, that the "hydrogenation catalyst" and "acid co-catalyst" need not be in the form of separate catalysts, but can be present together in the form of particles of a solid, bi-functional catalyst. In such a bi-functional catalyst, (i) any "hydrogenation catalyst," or component thereof, as described above, may be present as a hydrogenation-active constituent of such a bi-functional catalyst, and (ii) any "acid co-catalyst," or component thereof, as described above, may be present as an acidic constituent of such a bi-functional catalyst. For example, a bi-functional catalyst may comprise any of the one or more hydrogenation active metals described above (e.g., nickel), deposited on any of the solid, acid co-catalysts described above (e.g., a zeolite or a metal oxide). The hydrogenation active metal(s) may be present in such bi-functional catalyst, as a hydrogenation-active constituent, in the amounts given above (e.g., at least 5 wt-%, based on the bi-functional catalyst weight), or possibly lower amounts (e.g., at least 2.5 wt-%, based on the bi-functional catalyst weight), as a result of integrating the two catalysts. The solid, acid co-catalyst, as an acidic constituent, may have a density of Lewis acid sites in the ranges given above (e.g., from 50 to 2000 µmol/g), or possibly lower ranges (e.g., from 25 to 1000), as a result of integrating the two catalysts.

Acid co-catalysts, and particularly Lewis acids, may be homogeneous in the reaction mixture, generally such that both the co-catalyst and reaction mixture are in the liquid phase (e.g., in the case of the co-catalyst being solubilized). According to a particular embodiment, the co-catalyst is solubilized in an aqueous liquid reaction mixture, comprising aqueous ammonia (ammonium hydroxide) as the aminating agent. Representative soluble acid co-catalysts are metallic trifluoromethylsulfonates, otherwise known as metal triflates. Specific examples include the triflates of the 15 lanthanide elements, as well as triflates of scandium and yttrium. According to a particular embodiment, a triflate co-catalyst may be selected from the group consisting of bismuth (Bi) triflate, gallium (Ga) triflate, copper (Cu) triflate, europium (Eu) triflate, silver (Ag) triflate, indium (In) triflate, cerium (Ce) triflate, gadolinium (Gd) triflate, erbium (Er) triflate, aluminum (Al) triflate, and mixtures of any two or more of these triflates. Other examples of co-catalysts that act as homogeneous Lewis acids include ammonium compounds other than ammonium hydroxide when used as the aminating agent. Ammonium acetate and ammonium chloride are exemplary.

Whether or not the acid co-catalyst is solid (heterogeneous) in the reaction mixture, liquid (homogeneous) in the reaction mixture, solid and separate from the hydrogenation catalyst, or solid and integrated with the hydrogenation catalyst, improvements may be obtained according to the referenced application in methods for the reductive amination of glycolaldehyde to make MEA (or MEA and taurine, by using but a portion of the MEA so formed to synthesize taurine), resulting from the use of the acid co-catalyst. Particular improvements are increased selectivity to the desired compound, monoethanolamine, and/or decreased selectivity to undesired byproducts, such as the dimerized byproduct, diethanolamine, and/or the hydrogenated byproduct, ethylene glycol. The amount of acid co-catalyst for obtaining a given effect (e.g., selectivity improvement) is dependent on the particular acid co-catalyst used and given set of reductive amination conditions, and with the knowledge gained from the present disclosure, those skilled in the art can determine a suitable amount in each case. Generally, any acid co-catalyst described above, or combination of acid co-catalysts, may be present in the reaction mixture, including the hydrogenation catalyst and solvent such as water, in an amount, or combined amount, generally from 0.1 wt-% to 99 wt-%. More typically, co-catalyst(s) may be present in an amount or combined amount from 0.1 wt-% to 20 wt-%, such as from 0.3 wt-% to 15 wt-% or from 0.5 wt-% to 10 wt-%. In the case of a continuous process, the acid co-catalyst may be present in an amount needed to achieve a weight hourly space velocity (WHSV) with respect to this catalyst, as described below. The acid co-catalyst, as well as the hydrogenation catalyst, and optionally a bi-functional catalyst having integrated constituents as described herein, can be prepared by any method known in the art including, for example, impregnation/incipient wetness, co-precipitation, or hydrothermal.

In certain other embodiments, we have found advantageously that where the reductive amination catalyst is a catalytic combination including from 1 to 99 percent by weight (of the total weight of the catalytic combination) of a nickel catalyst component and the remainder (from 99 to 1 percent by weight) is an acidic co-catalyst component, then at certain reaction temperatures for carrying out the reductive amination using such a combination, the formaldehyde removal step 16 may be omitted and the composition 10 may be used directly in the reductive amination step 20.

In this particular catalytic combination, however, the nickel catalyst or catalysts used in the nickel catalyst component of the combination is (or are) not a sponge metal nickel catalyst (or catalysts). More preferably, the nickel catalyst component will comprise fifty percent by weight or less of the combination, more preferably will be forty percent by weight or less of the combination and still more preferably will be thirty five percent by weight or less of the combination, the objective in all cases with these nickel/acidic co-catalyst combinations being to provide a balance of hydrogenation activity and acidity in the combination such that substantially no tendency to form diethanolamine or ethylene glycol is exhibited in the reductive amination and such that the formaldehyde does not appreciably react to form unwanted byproducts in the course of the reductive amination. Typically, this balance is observed for catalytic combinations of nickel with an acidic co-catalyst component wherein the nickel is fifty percent or less at reductive amination reaction temperatures of up to 85 degrees Celsius, while catalytic combinations including a greater proportion of the nickel component may require lower reductive amination reaction temperatures to accomplish these objectives. The catalytic combination may, as demonstrated in the examples following, be comprised of a physical mixture of one or more nickel catalysts and one or more acidic co-catalysts or may result from co-precipitating these materials in the indicated proportions in the combination.

Representative processes according to this first aspect wherein taurine is principally desired, or wherein monoethanolamine and taurine are desired in preference to diethanolamine, are therefore characterized by high selectivities to monoethanolamine. According to particular embodiments, glycolaldehyde may be converted with a molar selectivity to monoethanolamine of 45% or more to 98% or less, in other embodiments of 55% or more to 94% or less, and in other embodiments of 70% or more to 90% or less. In particular embodiments, the molar selectivity to MEA is at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98 percent. Such selectivities are further preferably according to this first aspect associated with comparably low selectivities to the dimerized byproduct, diethanolamine. According to particular embodiments, glycolaldehyde may be converted with a molar selectivity to diethanolamine of less than 20%, less than 10%, or less than 5%, for example, less than 20, 19, 18, 17, 16, 15, 14, 13, 12, 11, 10, 9, 8, 7, 6 or 5 percent. Alternatively, the selectivity improvement may be characterized with respect to a reference molar selectivity, obtained from a reference process in which all reductive amination conditions (e.g., pressure, temperature, residence time, feeds (including aminating agent), catalyst(s), etc.) are identical, except for the absence of the acid co-catalyst. According to particular embodiments, glycolaldehyde may be converted with a molar selectivity to monoethanolamine, which exceeds a reference molar selectivity by at least 3%. That is, in the case of a reference molar selectivity of 50%, the use of the acid co-catalyst results in a molar selectivity that is increased to at least 53%. In other embodiments, glycolaldehyde may be converted with a molar selectivity to monoethanolamine, which exceeds a reference molar selectivity by at least 5%, or even at least 10%, for example, at least 3, 4, 5, 6, 7, 8, 9 or 10 percent. Those skilled in the art will appreciate that even modest increases in selectivity can potentially result in substantial economic benefits on the commercial scale.

The molar selectivities described above are preferably obtained at high levels of conversion of glycolaldehyde. According to particular embodiments, the glycolaldehyde conversion may be at least 85%, at least 90%, at least 95%, or even at least 99%, thus at least 85, 86, 87, 88, 89, 90, 91, 92, 93, 94, 95, 96, 97, 98 or 99 percent. Accordingly, representative yields of monoethanolamine may be the same or substantially the same as the molar selectivity ranges given above, such as 45% or more to 98% or less, in other embodiments from 55% or more to 94% or less, or in other embodiments from 70% or more to 90% or less of the theoretical yield obtainable, given that yield is determined as the product of conversion and selectivity.

Typical reductive amination conditions for the use of the other reductive amination catalysts described above, or using the particular catalytic combination described above for optionally omitting the formaldehyde removal step 16, include an elevated hydrogen partial pressure, such as at least 3 megapascals (MPa) (435 psi). This hydrogen pressure may be contained in a reactor that is used for the contacting of the feed (e.g., an aqueous feed comprising glycolaldehyde) and an aminating agent (e.g., aqueous ammonia), with the catalysts or bi-functional catalyst as described above or with the catalytic combination including less than fifty percent by total weight of a nickel catalyst component and further including an acidic co-catalyst component to obtain this product. The reaction mixture, to which the feed and aminating agent are added and from which a product mixture is withdrawn (e.g., following separation from the catalyst(s)) is preferably aqueous and comprises dissolved hydrogen under the reductive amination conditions.

The aminating agent may be aqueous ammonia, or in addition or alternatively, may comprise gaseous ammonia that may be added batchwise or continuously to the reactor, for example it may be added, in the case of continuous operation, with hydrogen or a recycle gas stream comprising hydrogen. The addition of gaseous ammonia will generally cause the in situ formation of aqueous ammonia in the presence of an aqueous reaction mixture. Other possible aminating agents include primary and secondary amines of the formula $NHR^1R^2$, wherein at least one of $R^1$ and $R^2$ is a $C_1$-$C_3$ alkyl group. The glycolaldehyde and aminating agent may be charged to the reactor batchwise, or otherwise continuously added to the reactor, with a molar excess of the aminating agent, for example, with an aminating agent: glycolaldehyde molar ratio of from 2:1 to 20:1 or from 5:1 to 15:1.

Reductive amination conditions, under which the reaction mixture is maintained during the production of monoethanolamine, typically again include an elevated pressure and hydrogen partial pressure. Representative absolute reactor pressures are in the range generally from 2.07 MPa (300 psi) to 24.1 MPa (3500 psi), typically from 3.45 MPa (500 psi) to 20.7 MPa (3000 psi), and often from 5.17 MPa (750 psi) to 10.3 MPa (1500 psi). The reactor pressure may be generated predominantly or substantially from hydrogen, such that these ranges of total pressure may also correspond to ranges of hydrogen partial pressure. However, the presence of gaseous ammonia or other aminating agent, as well as other gaseous species vaporized from the reaction mixture, may result in the hydrogen partial pressure being reduced relative to these total pressures, such that, for example, the hydrogen partial pressure may range generally from 1.38 MPa (200 psi) to 22.4 MPa (3250 psi), typically from 3.00 MPa (435 psi) to 20.0 MPa (2901 psi), and often from 4.82 MPa (700 psi) to 9.31 MPa (1350 psi).

Other reductive amination conditions, present in the reactor, include a temperature generally from 20° C. (68° F.) to 200° C. (392° F.), and typically from 50° C. (122° F.) to 150° C. (302° F.). The reaction time, i.e., time at which the reaction mixture is maintained under conditions of pressure and temperature at any target values or target sub-ranges within any of the ranges of pressure and temperature given above (e.g., a target, total pressure value of 8.27 MPa (1200 psi) and a target temperature of 85° C. (185° F.), is from 0.5 hours to 24 hours, and preferably from 1 hour to 5 hours, in the case of a batchwise reaction. For a continuous process, these reaction times correspond to reactor residence times. An additional parameter that is relevant for a continuous process is weight hourly space velocity (WHSV), which is understood in the art as the weight flow of the feed (e.g. aqueous feed comprising glycolaldehyde and $NH_4OH$) to a reactor, divided by the catalyst weight (e.g., combined weight of the hydrogenation catalyst and acid co-catalyst, or weight of a bi-functional catalyst or of the catalytic non-sponge nickel/acidic co-catalyst combination). This parameter therefore represents the equivalent catalyst bed weight of the feed processed every hour, and it is related to the inverse of the reactor residence time. According to representative embodiments, the reductive amination conditions include a WHSV generally from $0.01 \text{ hr}^{-1}$ to $20 \text{ hr}^{-1}$, and typically from $0.05 \text{ hr}^{-1}$ to $5 \text{ hr}^{-1}$. However, with respect to the acid co-catalyst alone, these ranges may be higher, for example generally from $0.02 \text{ hr}^{-1}$ to $40 \text{ hr}^{-1}$, and typically from $0.1 \text{ hr}^{-1}$ to $10 \text{ hr}^{-1}$.

As described above, a continuous process, such as a continuous fixed bed process, may be more compatible with a heterogeneous acid co-catalyst (e.g., comprising a molecular sieve, activated carbon, metal oxide, or resin, having a requisite density of Lewis acid sites). Such a continuous process may be performed by continuous feeding of glycolaldehyde, aminating agent, and hydrogen to the reaction mixture comprising the catalyst(s) and contained within the reactor, and continuous withdrawal, from the reactor, of a reductive amination product mixture 26 comprising monoethanolamine and substantially free of the catalyst(s). Though not included in the schematic process shown in FIG. 1, those skilled in the art will nevertheless appreciate that this product mixture may then be further processed by separating portions of the product mixture to purify and recover the monoethanolamine therefrom and optionally recycle unconverted reactants, such as the aminating agent and/or hydrogen.

According to one embodiment, the reductive amination product mixture 26 may be subjected to flash separation to separate a primarily hydrogen-containing vapor phase, at least portion of which (e.g., following the removal of a purge stream to prevent excessive accumulation of unwanted impurities) may provide the recycle gas stream, described above. The liquid phase recovered from the flash separation and also comprising the desired monoethanolamine, may be subjected to any of a number of possible separation steps, including one or more of phase separation, extraction (e.g., using an organic solvent having preferential affinity for monoethanolamine), and distillation, sequentially in any order. Extraction and distillation may alternatively be combined in a single, extractive distillation step. As with the recycle gas stream, any separated liquid products (e.g., aminating agent and/or unconverted glycolaldehyde) may likewise be recycled to the reactor. Whether performed batchwise or continuously, particular embodiments relate to methods for producing monoethanolamine, comprising performing a reductive amination of glycolaldehyde, added to an aqueous reaction mixture with aqueous ammonia as a reactant. This may be performed by contacting this reaction mixture and hydrogen with the above-described hydrogenation catalyst/acid co-catalyst system or the formaldehyde-tolerant catalytic combination including a nickel catalyst and an acidic co-catalyst component under reductive amination conditions, also as described above. Advantageously, the reductive amination efficiently produces monoethanolamine according to any of the conversion, selectivity, and yield performance criteria described above, such as a yield of at least 70% of a theoretical yield.

In certain embodiments of the invention, as already mentioned, monoethanolamine may be co-produced with taurine by using but a portion of the MEA so formed in stream 26 (suggested by stream 28 in FIG. 1, with the remaining MEA being diverted for sale or alternate uses in stream 30) to synthesize the taurine by first sulfating the MEA in stream 28 in step 32 to produce 2-aminoethyl hydrogen sulfate ester (34), and then sulfonating the 2-aminoethyl hydrogen sulfate ester in a sulfonation step 36 to produce a taurine product 38.

Sulfation and sulfonation steps 32 and 36 are known to the art for converting MEA to taurine (or, 2-aminoethanesulfonic acid). For example, Bondareva et al., "Synthesis of Taurine", Pharmaceutical Chemistry Journal, vol. 42, No. 3, pp. 142-144 (2008) describe that taurine had been made in the United States and Japan previously by other methods from other feeds (namely, isothionic acid salt, aziridine and haloethylamines), but report a method whereby monoethanolamine is first sulfated with sulfuric acid to provide 2-aminoethylsulfuric acid, then taurine is prepared therefrom by sulfonating the 2-aminoethylsulfuric acid with sodium sulfite. The sulfation step is more particularly performed with 75-80% sulfuric acid (schematically illustrated by stream 40), at reduced pressure and temperatures of 130 to 135 degrees Celsius, with vigorous stirring and with continuous and complete water removal to drive the reaction forward and provide the 2-aminoethylsulfuric acid as a powder that is of a sufficient purity to be used directly in the next step. Sulfonation takes place by sodium sulfite in aqueous solution (addition of the sodium sulfite, sulfonating agent being indicated schematically by stream 42), optimum yields of taurine being found at a 1.0:1.2 mole ratio of the 2-aminoethylsulfuric acid to sodium sulfite and with heating from 23 to 28 hours. The product mixture comprising taurine and sodium sulfate was then dehydrated by Bondareva et al., before a step to isolate the taurine in a pharmacopeic purity was begun using aqueous ammonia as an extractant for the taurine and then distilling off the ammonia to provide crystalline taurine (38) that could be further purified by recrystallization from water. United States Patent Application Publication No. 2015/0183731 to Hu is illustrative also in purporting to provide an improvement to the MEA-based process as described in Bondareva et al as well as the variants described in other publications (namely, JPS608254, CN 101100449A and CN102633689), in the form of a cyclic process of reacting MEA, sulfuric acid and ammonium sulfite in the presence of additives to inhibit the hydrolysis of the 2-aminoethylsulfuric acid intermediate. More particularly, Hu claims dramatic yield improvements with reduced waste products, by carrying out the sulfonation step in a buffering system at a pH of from 6.0 to 8.0 (with a preferred buffering system of ammonium bisulfite and excess ammonium sulfite), further by the use of hydrolysis inhibitors (preferred examples being MEA, diethanolamine (DEA), triethanolamine (TEA) and dimethylaminoethanol), and through converting residual MEA in the crystalline mother liquor to additional quantities of the intermediate that are recycled to react with ammonium sulfite and provide more taurine.

In other embodiments of the invention wherein diethanolamine is a desired co-product with monoethanolamine and taurine on the one hand, or with taurine alone on the other (so that all MEA produced in the reductive amination step is, to the extent economically practicable, utilized for the production of taurine 38 in FIG. 1), the reductive amination step 20 can in certain embodiments be carried out, preferably following a formaldehyde removal step 16, using the catalysts described above as to be more preferred for producing DEA, and an MEA/DEA separation step 44 is included after the reductive amination step 20 to provide an additional diethanolamine product stream 46. The separation of diethanolamine from the reductive amination product mixture 26 can be by means of distillation as presently practiced in the manufacture of MEA, DEA and TEA from non-renewable resources.

Thus, glycolaldehyde (including forms of this compound as described above) in the reduced formaldehyde pyrolysis product mixture 18 is in certain such embodiments reacted in step 20 with an aminating agent 22 and a source of hydrogen 24 in the presence of a noble metal-containing hydrogenation catalyst under reductive amination conditions, to produce the diethanolamine (e.g., in a reductive amination product mixture 26 from which the diethanolamine may be recovered). A representative hydrogenation catalyst is a noble metal-containing catalyst, meaning that it comprises at least one noble metal.

For example, the hydrogenation catalyst may comprise platinum or palladium as a noble metal, or may comprise both of these noble metals. The hydrogenation catalyst may comprise either or both of these noble metals, or other noble metals, in an amount, or in a combined amount, generally from 0.1 wt-% to 15 wt-%, and typically from 0.5 wt-% to 10 wt-%, based on the weight of the catalyst. Regardless of the amount, the hydrogenation catalyst may be a solid supported noble metal-containing catalyst, meaning that the noble metals are disposed on a solid support, which may be substantially refractory (inert) under reductive amination conditions, or which may itself be functional (e.g., in the case of providing acidic or basic sites to provide or promote catalytic activity). Carbon, including activated carbon, is an exemplary solid support.

Noble metals are understood as referring to a class of metallic elements that are resistant to oxidation. In representative embodiments, the at least one noble metal of the hydrogenation catalyst may be selected from the group consisting of platinum (Pt), rhodium (Rh), ruthenium (Ru), palladium (Pd), silver (Ag), osmium (Os), iridium (Jr), and gold (Au), with the term "consisting of" being used merely to denote group members, according to a specific embodiment, from which the noble metal(s) are selected, but not to preclude the addition of other noble metals and/or other metals generally. Accordingly, a hydrogenation catalyst comprising a noble metal embraces a catalyst comprising at least two noble metals, as well as a catalyst comprising at least three noble metals, and likewise a catalyst comprising two noble metals and a third, non-noble metal such as a promoter metal (e.g., a transition metal). According to preferred embodiments, the noble metal(s) is/are present in an amounts, or combined amounts, within the ranges given above. Alternatively, in the case of at least two noble metals being present, they may each independently be present in amounts from 0.05 wt-% to 12 wt-%, from 0.3 wt-% to 10 wt-%, or from 1 wt-% to 7.5 wt-%, based on the weight of the catalyst. For example, a representative hydrogenation catalyst may comprise the two noble metals Pt and Pd, and the Pt and Pd may independently be present in an amount within any of these ranges (e.g., from 1 wt-% to 7.5 wt-%). That is, either the Pt may be present in such an amount, the Pd may be present in such an amount, or both Pt and Pd may be present in such amounts.

In representative embodiments, a single noble metal (e.g., either Pt or Pd), or two noble metals (e.g., both Pt and Pd) may be substantially the only noble metals present in the hydrogenation catalyst, such that, for example, any other noble metal(s) is/are present in an amount or a combined amount of less than 0.1 wt-%, or less than 0.05 wt-%, based on the weight of the hydrogenation catalyst. In further representative embodiments, a single noble metal, or two noble metals, are substantially the only metals present in the hydrogenation catalyst, with the exception of metals that may be present in the solid support (e.g., such as aluminum being present in the solid support as aluminum oxide). Therefore, in the case of support comprising substantially all carbon, the single noble metal, or two noble metals, may be substantially the only metals present. For example, any other metal(s), besides the single noble metal, or two noble metals, and metals of the solid support (if any), may be present in an amount or a combined amount of less than 0.1 wt-%, or less than 0.05 wt-%, based on the weight of the hydrogenation catalyst. Any metals present in the catalyst, including noble metal(s), may have a metal particle size in the range generally from 0.3 nanometers (nm) to 20 nm, typically from 0.5 nm to 10 nm, and often from 1 nm to 5 nm.

The hydrogenation-active, noble metal(s) of representative hydrogenation catalysts may be disposed or deposited on a solid support, which is intended to encompass catalysts in which the noble metal(s) is/are on the support surface and/or within a porous internal structure of the support. Therefore, in addition to such hydrogenation-active metal(s), representative hydrogenation catalysts may further comprise a solid support, with exemplary solid supports comprising carbon and/or one or more metal oxides. Exemplary metal oxides are selected from the group consisting of aluminum oxide, silicon oxide, titanium oxide, zirconium oxide, magnesium oxide, strontium oxide, tin oxide, etc. The solid support may comprise all, or substantially all of the one or more of such metal oxides, for example such that the one or more metal oxides are present in an amount, or combined amount, of at least 95% by weight of the solid support. Alternatively, carbon, such as activated carbon, may be present in an amount of at least 95% by weight, or at least 99% by weight, of the solid support. Activated carbon refers to forms of carbon following any of a number of possible treatments (e.g., high temperature steaming) to increase porosity. Activated carbon also refers to forms obtained by chemical treatment (e.g., an acid or a base) to alter properties such as the concentration of acid sites.

The noble metal(s) may be incorporated in the solid support according to known techniques for catalyst preparation, including sublimation, impregnation, or dry mixing. In the case of impregnation, an impregnation solution of a soluble compound of one or more of the noble metals in a polar (aqueous) or non-polar (e.g., organic) solvent may be contacted with the solid support, preferably under an inert atmosphere. For example, this contacting may be carried out, preferably with stirring, in a surrounding atmosphere of nitrogen, argon, and/or helium, or otherwise in a non-inert atmosphere, such as air. The solvent may then be evaporated from the solid support, for example using heating, flowing gas, and/or vacuum conditions, leaving the dried, noble metal-impregnated support. The noble metal(s) may be impregnated in the solid support, such as in the case of two noble metals being impregnated simultaneously with both being dissolved in the same impregnation solution, or otherwise being impregnated separately using different impregnation solutions and contacting steps. In any event, the noble metal-impregnated support may be subjected to further preparation steps, such as washing with the solvent to remove excess noble metal(s) and impurities, further drying, calcination, etc. to provide the hydrogenation catalyst.

The solid support itself may be prepared according to known methods, such as extrusion to form cylindrical particles (extrudates) or oil dropping or spray drying to form spherical particles. Regardless of the specific shape of the solid support and resulting catalyst particles, the amounts of noble metal(s) being present in the hydrogenation catalyst, as described above, refer to the weight of such noble metal(s), on average, in a given catalyst particle (e.g., of any shape such as cylindrical or spherical), independent of the particular distribution of the noble metals within the particle. In this regard, it can be appreciated that different preparation methods can provide different distributions, such as deposition of the noble metal(s) primarily on or near the surface of the solid support or uniform distribution of the noble metal(s) throughout the solid support. In general, weight percentages described herein, being based on the weight of the solid support or otherwise based on the weight of hydrogenation catalyst, can refer to weight percentages in a single catalyst particle but more typically refer to average weight percentages over a large number of catalyst particles, such as the number in a reductive amination reactor that form a catalyst bed as used in processes described herein.

Generally, any hydrogenation catalyst described above, or combination of catalysts, may be present in the reaction mixture, including the solvent such as water, in an amount, or combined amount, from 0.1 wt-% to 10 wt-%, such as from 0.3 wt-% to 5 wt-% or from 0.5 wt-% to 3 wt-%. In the case of a continuous process, the hydrogenation catalyst may be present in an amount needed to achieve a weight hourly space velocity (WHSV) as described below.

Representative processes are therefore characterized by comparatively high selectivities to diethanolamine, relative to conventional processes. According to particular embodiments, glycolaldehyde may be converted with a molar selectivity to diethanolamine of from 30% or more to 85% or less, in other embodiments with a molar selectivity of from 40% or more to 80% or less, and in still other embodiments from 50% or more to 75% or less, for example, a molar selectivity of at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 up to 85%. Such selectivities may be correspondingly associated with lower selectivities to monoethanolamine and thus to the taurine that can be made therefrom, as may be indicated by prevailing economic and commercial considerations. According to particular embodiments, glycolaldehyde may be converted with a molar selectivity to monoethanolamine of less than 35%, less than 25%, or less than 15%, for example, less than 35, 34, 33, 32, 31, 30, 29, 28, 27, 26, 25, 24, 23, 22, 21, 20, 19, 18, 17, 16 or 15% to monoethanolamine. In yet other embodiments, the molar selectivity to diethanolamine may be at least 1.5 times, or at least two times, the molar selectivity to monoethanolamine. Alternatively, the selectivity improvement may be characterized with respect to a reference molar selectivity, obtained from a reference process in which all reductive amination conditions (e.g., pressure, temperature, residence time, feeds (including aminating agent), catalyst(s), etc.) are identical, except for the replacement of the noble metal-containing hydrogenation catalyst with an equal weight of the conventional catalyst, Raney nickel. This material is namely a type of sponge nickel catalyst that is further characterized by being a fine-grained solid composed mostly of nickel that is present as a nickel-aluminum alloy.

According to particular embodiments, glycolaldehyde may be converted with a molar selectivity to diethanolamine, which exceeds a reference molar selectivity by at least 15%. That is, in the case of a reference molar selectivity of 15%, the use of the hydrogenation catalyst compared to Raney nickel results in a molar selectivity that is increased to at least 30%. In other embodiments, glycolaldehyde may be converted with a molar selectivity to diethanolamine, which exceeds a reference molar selectivity by at least 20%, or even at least 30%. Those skilled in the art will appreciate that even modest increases in selectivity can potentially result in substantial economic benefits on the commercial scale.

The molar selectivities described above may be obtained at high levels of conversion of glycolaldehyde. According to particular embodiments, the glycolaldehyde conversion may be at least 85%, at least 90%, at least 95%, or even at least 99%. Accordingly, representative yields of diethanolamine may be the same or substantially the same as the molar selectivity ranges given above, such as at least 30% (e.g., from 30% to 85%), at least 40% (e.g., from 40% to 80%), or at least 50% (e.g., from 50% to 75%), of the theoretical yield obtainable, given that yield is determined as the product of conversion and selectivity.

Typical reductive amination conditions for the use of the catalysts referenced for production of diethanolamine in particular as a co-product include an elevated hydrogen partial pressure, such as at least 3 megapascals (MPa) (435 psi), which, in combination with the noble metal-containing hydrogenation catalyst, provide a reductive amination environment for carrying out the conversion of glycolaldehyde, selectively to the desired co-product diethanolamine. This hydrogen pressure may be contained in a reactor that is used for the contacting of the feed (e.g., an aqueous feed comprising glycolaldehyde) and an aminating agent (e.g., aqueous ammonia), with the noble metal-containing hydrogenation catalyst as described above, to obtain this product. The reaction mixture, to which the feed and aminating agent are added and from which a product mixture is withdrawn (e.g., following separation from the catalyst(s)) is preferably aqueous and comprises dissolved hydrogen under the reductive amination conditions. In addition, or alternatively, to aqueous ammonia, the aminating agent may otherwise comprise gaseous ammonia that may be added batchwise or continuously to the reactor, for example it may be added, in the case of continuous operation, with hydrogen or a recycle gas stream comprising hydrogen. The addition of gaseous ammonia will generally cause the in situ formation of aqueous ammonia in the presence of an aqueous reaction mixture. Other possible aminating agents include primary and secondary amines of the formula $NHR^1R^2$, wherein at least one of $R^1$ and $R^2$ is a $C_1$-$C_3$ alkyl group. The glycolaldehyde and aminating agent may be charged to the reactor batchwise, or otherwise continuously added to the reactor, with a molar excess of the aminating agent, for example, with an aminating agent:glycolaldehyde molar ratio of from 2:1 to 20:1 or from 5:1 to 15:1.

Reductive amination conditions, under which the reaction mixture is maintained during the production of a reductive amination product mixture 26 containing relatively more of the desired diethanolamine co-product, include an elevated pressure and hydrogen partial pressure. Representative absolute reactor pressures are in the range generally from 2.07 MPa (300 psi) to 24.1 MPa (3500 psi), typically from 3.45 MPa (500 psi) to 20.7 MPa (3000 psi), and often from 5.17 MPa (750 psi) to 10.3 MPa (1500 psi). The reactor pressure may be generated predominantly or substantially from hydrogen, such that these ranges of total pressure may also correspond to ranges of hydrogen partial pressure. However, the presence of gaseous ammonia or other aminating agent, as well as other gaseous species vaporized from the reaction mixture, may result in the hydrogen partial pressure being reduced relative to these total pressures, such that, for example, the hydrogen partial pressure may range generally from 1.38 MPa (200 psi) to 22.4 MPa (3250 psi), typically from 3.00 MPa (435 psi) to 20.0 MPa (2901 psi), and often from 4.82 MPa (700 psi) to 9.31 MPa (1350 psi).

Other reductive amination conditions, present in the reactor, include a temperature generally from 20° C. (68° F.) to 200° C. (392° F.), and typically from 50° C. (122° F.) to 150° C. (302° F.). The reaction time, i.e., time at which the reaction mixture is maintained under conditions of pressure and temperature at any target values or target sub-ranges within any of the ranges of pressure and temperature given above (e.g., a target, total pressure value of 8.27 MPa (1200 psi) and a target temperature of 85° C. (185° F.), is from 0.5 hours to 24 hours, and preferably from 1 hour to 5 hours, in the case of a batchwise reaction. For a continuous process, these reaction times correspond to reactor residence times. An additional parameter that is relevant for a continuous process is weight hourly space velocity (WHSV), which is understood in the art as the weight flow of the feed (e.g. aqueous feed comprising glycolaldehyde and $NH_4OH$) to a reactor, divided by the weight of the catalyst, in this case the noble metal-containing hydrogenation catalyst. This parameter therefore represents the equivalent catalyst bed weight of the feed processed every hour, and it is related to the inverse of the reactor residence time. According to representative embodiments, the reductive amination conditions include a WHSV generally from 0.01 $hr^{-1}$ to 20 $hr^{-1}$, and typically from 0.05 $hr^{-1}$ to 5 $hr^{-1}$.

A continuous process involving a heterogeneous (solid) hydrogenation catalyst may be performed by continuous feeding of glycolaldehyde, aminating agent, and hydrogen to the reaction mixture comprising the catalyst and contained within the reactor, and continuous withdrawal, from the reactor, of a reductive amination product mixture 26 comprising diethanolamine that is substantially free of the catalyst. This product mixture may, again, then be further processed in a similar manner as described with reference to the desired production of more MEA, by separating portions of the product mixture 26 to purify and recover the diethanolamine and optionally recycle unconverted reactants, such as the aminating agent and/or hydrogen. According to one embodiment, the product mixture may be subjected to flash separation to separate a primarily hydrogen-containing vapor phase, at least portion of which (e.g., following the removal of a purge stream to prevent excessive accumulation of unwanted impurities) may provide the recycle gas stream, described above. The liquid phase recovered from the flash separation and also comprising the desired diethanolamine, may be subjected to any of a number of possible separation steps, including one or more of phase separation, extraction (e.g., using an organic solvent having preferential affinity for monoethanolamine), and distillation, sequentially in any order. Extraction and distillation may alternatively be combined in a single, extractive distillation step. As with the recycle gas stream, any separated liquid products (e.g., aminating agent and/or unconverted glycolaldehyde) may likewise be recycled to the reactor.

The following, non-limiting examples of features and combinations of features addressed above collectively further illustrate the present invention:

Example 1

Nickel-zirconia particles were prepared through a co-precipitation technique using a tetramethylammonium hydroxide solution. An aqueous solution of 3.0 g of a Ni-salt ($Ni(NO_3)_2$) and 3.0 g of a Zr-salt ($ZrO(NO_3)_2$) in 15 ml water was first prepared. Tetramethylammonium hydroxide solution was then added dropwise to a beaker containing the aqueous Ni salt/Zr salt solution, with constant stirring by a magnetic stirrer. A gel was observed to form, and further addition of the tetramethylammonium hydroxide solution provided a precipitate that settled out at a pH of about 9.0. The precipitate was washed with water several times, then air dried at 80° C. for 24 hours. The obtained dried green sample was then calcined at 550° C. for 5 hours. The resultant calcined Ni—$ZrO_2$ black solid was reduced at 450 degrees Celsius for one hour with $H_2$, then transferred to a nitrogen protected atmosphere.

Example 2

A pyrolysis product composition was first obtained by pyrolysis of an aqueous solution of 20 percent by weight of dextrose in water, in keeping with the above description. Table 1 describes the composition of the crude pyrolysis product composition in weight percents, as determined by HPLC:

TABLE 1

| Sample | Dextrose | Glyoxal | Pyruvaldehyde | Glycolaldehyde | Formaldehyde | Ethylene Glycol | Acetol |
|---|---|---|---|---|---|---|---|
| Feed | 0.01 | 0.337 | 0.136 | 5.995 | 0.562 | 0.286 | 1.018 |

0.56 g of a commercially available 1% Pt(Bi)/C catalyst was then added to 110 g of this crude pyrolysis product composition, and the mixture was stirred at room temperature and in exposure to air to assess the effectiveness of low temperature oxidation using this catalyst for accomplishing the selective oxidation of the formaldehyde in the crude pyrolysis product composition, with samples being drawn after 3 hours, after 72 hours, after 98 hours and finally after 120 hours' elapsed time. The extent of formaldehyde removal was determined by NMR.

The results were as shown in Table 2:

TABLE 2

| Elapsed Reaction Time (hrs) | Formaldehyde Removal (%) |
|---|---|
| 0 | 0 |
| 3 | 30 |
| 72 | 81 |
| 98 | 89 |
| 120 | 100 |

Example 3

0.51 grams of wet Ni-Zr material from Example 1 were added to a mixture of 11.0 grams of the crude pyrolysis product composition shown in Table 1 above and 15 ml of a 28% ammonia solution. The combination was then stirred at 65 degrees Celsius under a pressure of 1200 pounds per square inch of hydrogen for one hour. The resultant reductive amination product was cooled down to room temperature, and then filtered to remove the heterogeneous catalyst. A light brown liquid product was formed in which monoethanolamine was the major product and ethylene diamine was formed as a minor product, but with no evidence of the formation of either 2-(methylamino)ethanol or diethanolamine, based on GC and NMR analysis.

Comparative Example 1

0.8 grams of wet Raney Ni catalyst and 0.4 grams of $ZrO_2$ 31163 from Norpro were added to a mixture of 12.0 grams of the crude pyrolysis product composition shown in Table 1 above and 15 ml of 28% aqueous ammonia solution, in a 100 cc Hastelloy Parr reactor. The combination was again stirred at 65 degrees Celsius under 1200 psi hydrogen, for one hour. The reaction product was cooled down to room temperature, and then filtered out to remove the heterogeneous catalyst. The remaining light brown liquid reductive amination product mixture had monoethanolamine as its major product, ethylene diamine as a minor product but also showed the presence of the 2-(methylamino)ethanol byproduct from formaldehyde and of diethanolamine, based on GC and NMR analysis.

Example 4

To four grams of monoethanolamine and 6 grams of water was added 1 ml of concentrated (96.8%) $H_2SO_4$. After stirring for 30 minutes, water was removed and another 1 ml of the concentrated sulfuric acid added, resulting in a white solid. After adding 5 ml of water, the mass was filtered to provide a white solid that was identified as aminoethylene sulfonic ester (providing an 86% yield).

Example 5

6.2 grams of the aminoethylene sulfonic ester prepared in Example 4 and 6.04 grams of $Na_2SO_3$ were combined with 3 ml of an aqueous solution of ammonia in water (28% ammonium hydroxide) in a 100 cc Hastelloy Parr reactor. After purging the reactor twice with nitrogen, the reactor was then charged with 200 psi nitrogen and heated to 100 degrees Celsius for one hour with constant agitation by stirring at 1100 rpm. The reactor was cooled down to room temperature, and the contents filtered and evaporated to yield taurine in the form of a white solid, with a demonstrated 80% yield on NMR analysis.

Comparative Example 2

Ten grams of the crude pyrolysis product composition shown in Table 1 were combined with 1.5 grams of wet Raney nickel, sponge metal catalyst in 15 ml of 28% aqueous ammonia solution in a 100 cc Hastelloy Parr reactor. After purging the reactor twice with nitrogen, the reactor was then charged with 900 psi nitrogen and heated to 65 degrees Celsius for two hours with constant agitation by stirring at 1100 rpm. The reaction product was cooled down to room temperature, and then filtered out to remove the heterogeneous catalyst. The remaining generally colorless reductive amination product mixture provided monoethanolamine in 56.3% yield (mass basis) and 17% by weight of ethylene glycol, based on GC and NMR analysis.

Example 6

A number of resins were evaluated for their effectiveness in scrubbing formaldehyde from a crude pyrolysis product mixture containing typical products from the hydrous thermolysis of dextrose, by combining 200 mg of a given resin with 2 mL of the pyrolysis product mixture and stirring overnight at room temperature and pressure, then filtering the mixture and analyzing the filtrate by GC and HPLC. Results are shown in Table 3 below (alongside the 1% Pt(Bi)/C result from Example 2 above and the greensand result from Example 7 below which were generated using different pyrolysis product mixtures, but which results have been equivalently expressed below in Table 3 in terms of the beginning amounts of glycolaldehyde and formaldehyde in the pyrolysis product mixtures used in those Examples 2 and 7), and demonstrate that a Purolite® A110 macroporous polystyrenic weak base anion exchange resin having primary amine functionality is comparatively effective for removing formaldehyde from a crude product mixture from the hydrous thermolysis of dextrose:

TABLE 3

| Sample Name | Glycolaldehyde left, % | Formaldehyde, left, % |
|---|---|---|
| WA 30 WBA | 77.02% | 81.82% |
| CTA193 WBA | 83.65% | 89.09% |
| SD-2 mild WBA | 93.29% | 90.91% |
| CTA196 WBA | 78.80% | 83.64% |
| S7968 Adsorbent | 92.37% | 93.64% |
| A-103S | 80.11% | 83.64% |
| PAD550 Adsorbent | 94.91% | 94.55% |
| A110 WBA | 79.95% | 29.09% |
| PFA860 SBA | 91.75% | 93.64% |
| FPA 98 SBA | 93.91% | 92.73% |
| SP70 Adsorbent | 97.22% | 96.36% |
| HP2MGL Adsorbent | 96.22% | 96.36% |
| Pt(Bi)/C | 93.88% | 12.81% |
| Greensand | 94.63% | 97.91% |

Key:
WA 30 WBA—highly porous dimethylamine, tertiary amine functionality weak base anion exchange resin (Mitsubishi Chemical); CTA193—polystyrenic macroporous, weak base anion resin, tertiary amine functionality (Purolite); SD-2—tertiary amine functionality, macroporous styrene-divinylbenzene copolymer (Dow Chemical); CTA196—polystyrenic macroporous, weak base anion resin, tertiary amine functionality (Purolite); S 7968—nonfunctionalized, macroporous, monodisperse styrenic resin (Lanxess); A-103S—macroporous polystyrenic weak base anion resin with tertiary amine functionality (Purolite); A-110—macroporous polystyrenic weak base anion resin with primary amine functionality in free base ionic form; PAD 550—Purosorb™ PAD 550 nonionic macroporous polystyrenic adsorbent resin (Purolite); PFA-860—macroporous strong base anion resin, polyacrylic crosslinked with divinylbenzene and quaternary ammonium functional groups; FPA-98—Amberlite™ FPA98 Cl strong base anion, crosslinked acrylic macroreticular resin with quaternary amine functionality; SP 70—DIAION™ SEPABEADS™ SP 70 divinylbenzene-crosslinked polystyrenic adsorbent resin (Mitsubishi); HP2MGL—DIAION™ HP2MGL crosslinked polymethacrylate adsorbent resin (Mitsubishi)

Example 7

1.0 g of greensand (glauconite-containing sand) and 80.0 mL of a crude sugar pyrolysis product containing formaldehyde were combined with stirring for 2 hours at ambient conditions, then the mixture was filtered to isolate the greensand and the filtrate analyzed by NMR. More than 50% of the initial formaldehyde was removed.

Example 8

0.8 grams of wet Raney Ni catalyst and 0.4 grams of $ZrO_2$ 31163 from Norpro were added to a mixture of 12.0 grams of various treated and untreated pyrolysis product compositions (where the untreated pyrolysis product composition was as shown in Table 1 above) and 15 ml of 28% aqueous ammonia solution, in a 100 cc Hastelloy Parr reactor. The combination was again stirred at 65 degrees Celsius under 1200 psi hydrogen, for one hour. The reaction product was cooled down to room temperature, and then filtered out to remove the heterogeneous catalyst. The remaining light brown liquid reductive amination product mixture was then analyzed by GC, with the MEA yields based on the glycolaldehyde in the particular treated and untreated pyrolysis product compositions being shown in Table 4 as follows:

TABLE 4

| Treatment | MEA yield, % |
| --- | --- |
| None | 52.3 |
| Greensand | 18.2 |
| Pt(Bi)/C | 71.6 |
| A110 | 63.7 |

Example 9

A number of experiments were conducted to investigate the performance of various noble metal-containing hydrogenation catalysts in the reductive amination of glycolaldehyde. These catalysts were commercial, carbon-supported platinum and/or palladium catalysts, available from Evonik Industries, AG (Evonik) or Johnson Matthey Chemicals Company (JM), as indicated in Table 5 below. In each case, a feed comprising 5% glycolaldehyde dimer by weight in 28% aqueous ammonia solution was reacted, together with a fixed amount of noble metal-containing catalyst, in a high throughput screening batch reactor. A reference experiment was also performed with Raney nickel catalyst. The catalytic, reductive amination reactions were carried out in a sealed hydrogenolysis reactor at 85 degrees Celsius (185° F.) and under 8.27 MPa (1200 psi) hydrogen pressure for a 2 hour hold period. The reaction product, following separation from the solid catalyst, was analyzed by GC. The results demonstrated that yields and selectivities for diethanolamine could be enhanced significantly using noble metal-containing catalysts in place of Raney nickel.

TABLE 5

| Catalyst | Ethanolamine Yield-% | Diethanolamine Yield-% |
| --- | --- | --- |
| JM, 5% Pt/carbon | 10.03% | 42.42% |
| JM, 4% Pd, 1% Pt on carbon | 14.23% | 38.02% |
| Evonik E6 5% Pd/carbon | 13.81% | 31.03% |
| Evonik 5% Pd/carbon | 15.82% | 51.42% |
| Raney Ni | 36.31% | 14.40% |

Example 10

The following were charged to a 100 ml Parr reactor, made of Hastelloy: 1 gram of glycolaldehyde dimer, 1.5 grams of wet Raney, sponge nickel alloy (W.R. Grace & Co.), and 0.18 grams of aluminum tris(trifluoromethanesulfonate) (Al-Triflate) in 20 ml of $NH_4OH$ (28%). The reactor was purged twice with nitrogen, and then charged with 6.2 MPa (900 psi) hydrogen. The reaction mixture was stirred at 1100 rpm for 2 hours at 85 degrees Celsius (185° F.). After this time period, the reactor was cooled to room temperature, and the reaction mixture filtered to separate the nickel catalyst from a colorless product mixture. The calculated yields based on gas chromatograph (GC) analysis of this mixture were 93% monoethanolamine yield, 2% ethylene glycol yield, and 0.5% diethanolamine yield.

Example 11

A number of experiments were conducted to investigate the performance of various metal trifluoromethanesulfonates (triflates) as solubilized (homogeneous) co-catalysts with a Raney nickel catalyst, for the reductive amination of glycolaldehyde In each case, a feed comprising 5% glycolaldehyde dimer by weight in 28% aqueous ammonia solution was reacted, together with a fixed amount of Raney nickel and the metal triflate, in a high throughput screening batch reactor. Reference experiments were also performed without either of the Raney nickel catalyst or metal triflate co-catalyst, as well as with Raney nickel catalyst alone (in the absence of a metal triflate co-catalyst). The catalytic, reductive amination reactions were carried out in sealed reactors at 85 degrees Celsius (185° F.) and under 8.27 MPa (1200 psi) hydrogen pressure for a 2 hour hold period. The reaction product, following the separation from solid catalyst, was analyzed by GC. The results demonstrated that selectivity for monoethanolamine could be enhanced using metal triflates as co-catalysts, compared to the use of Raney nickel alone. The results, including glycolaldehyde conversion levels, selectivities to the byproducts propylene glycol and ethylene glycol, and selectivities to monoethanolamine, are shown in FIG. 1.

Example 12

Figure 2:
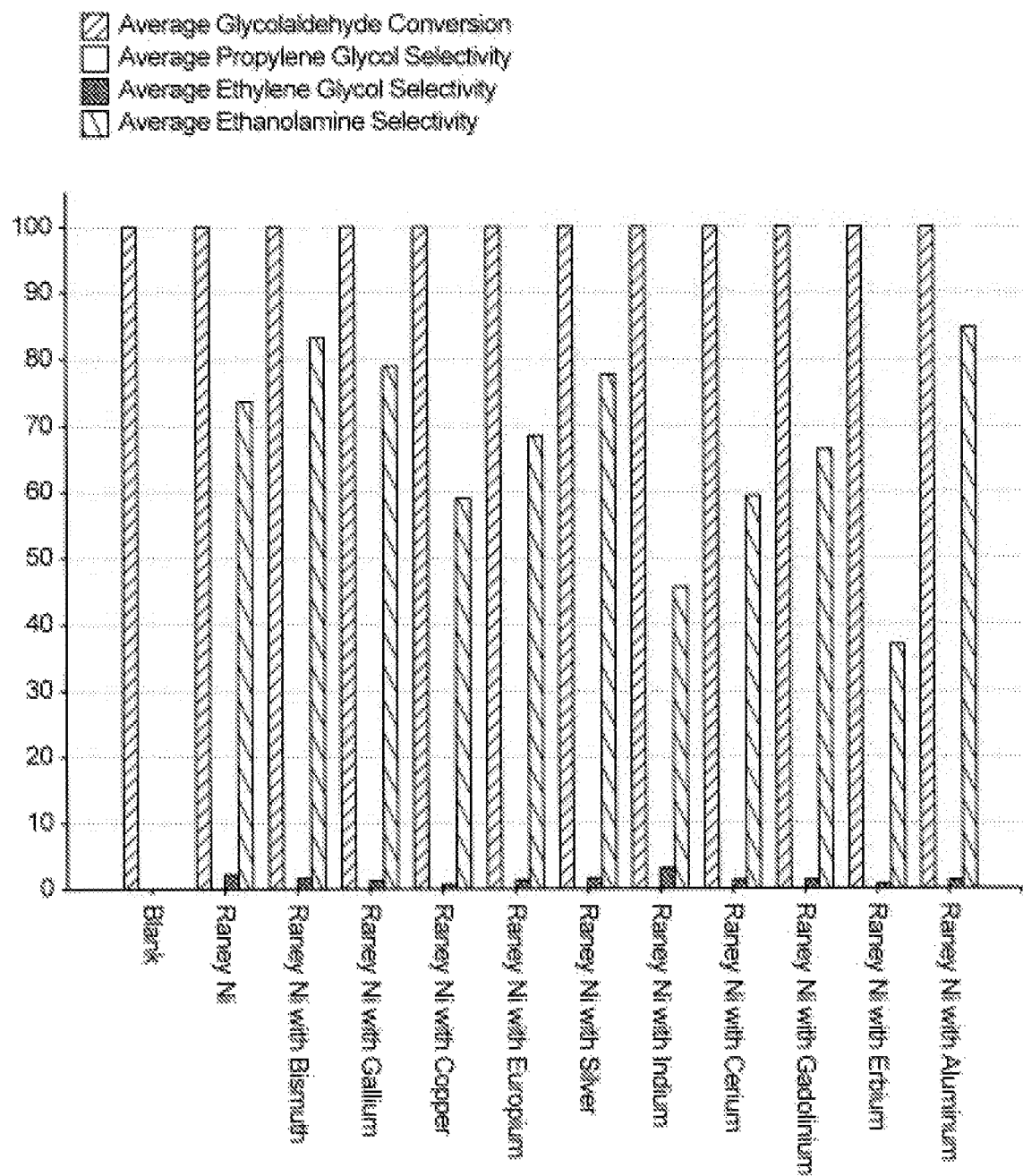
FIG. 2 is a bar graph of conversion and product selectivity values, obtained in experiments performing the reductive amination of glycolaldehyde (i) in the absence of a catalyst, (ii) in the presence of Raney nickel alone, and (iii) in the presence of both Raney nickel and a metal triflate as a co-catalyst.

A number of experiments were conducted to investigate the performance of various solid (heterogeneous) acid co-catalysts with a Raney nickel catalyst, for the reductive amination of glycolaldehyde. In each case, a feed comprising 5% glycolaldehyde dimer by weight in 28% aqueous ammonia solution was reacted, together with a fixed amount of Raney nickel and the solid acid co-catalyst, in a high throughput screening batch reactor. A reference experiment was also performed with Raney nickel catalyst alone (in the absence of a solid acid co-catalyst). The catalytic, reductive amination reactions were carried out in sealed reactors at 85 degrees Celsius (185° F.) and under 8.27 MPa (1200 psi) hydrogen pressure for a 2 hour hold period. The reaction product, following the separation from solid catalyst(s), was analyzed by GC. The results demonstrated that selectivity for, and consequently the yield of, monoethanolamine could be enhanced using solid acid co-catalysts, including zeolites and solid acids, such as acidified activated carbon and hydrated or acidic forms of tin oxide, compared to the use of Raney nickel alone. The ethanolamine and diethanolamine yield results for the various solid acid co-catalysts are shown in FIG. 2.

Example 13

Figure 3:
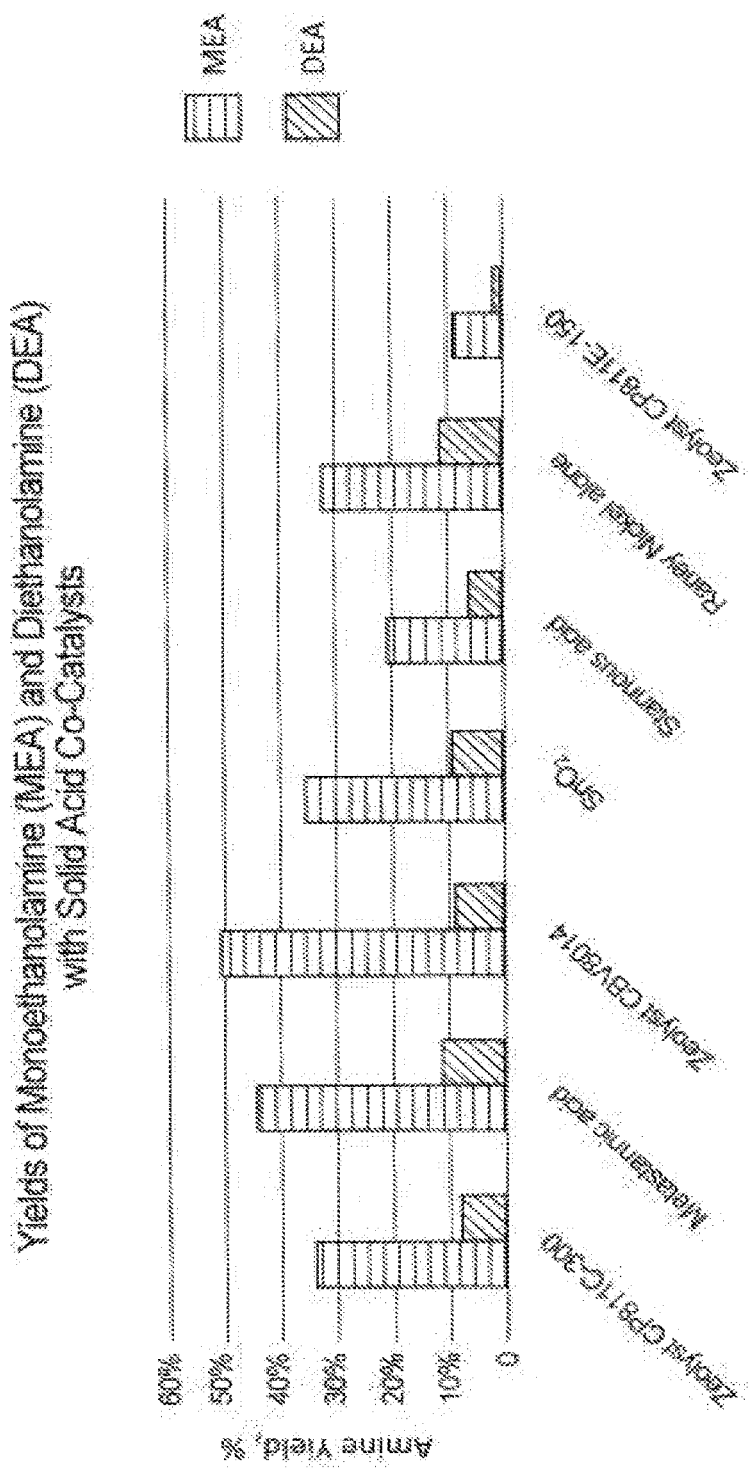
FIG. 3 is a bar graph of monoethanolamine and diethanolamine yield values, obtained in experiments performing the reductive amination of glycolaldehyde (i) in the presence of Raney nickel alone, and (ii) in the presence of both Raney nickel and various solid acid co-catalysts.
Figure 4:
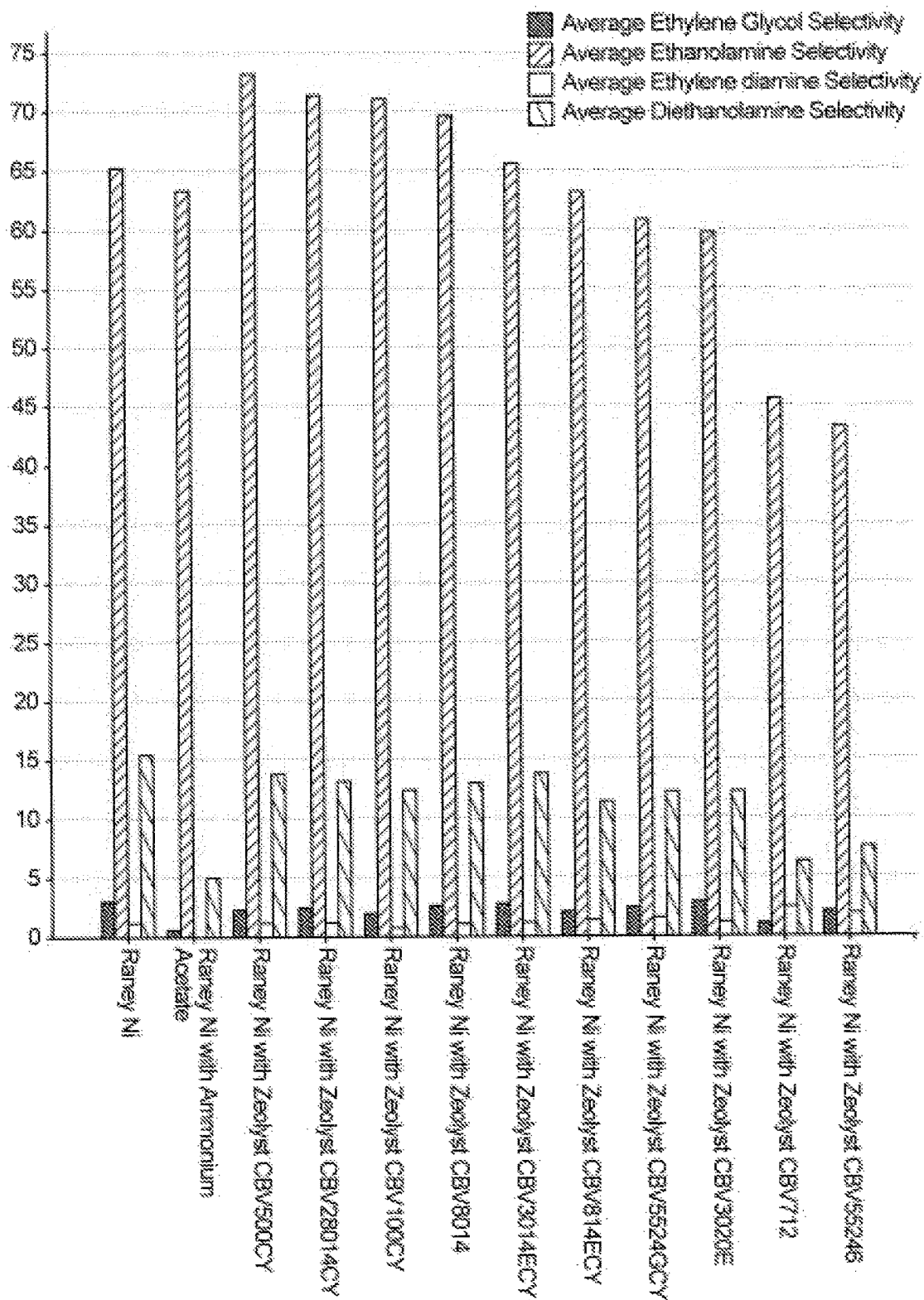
FIG. 4 is a bar graph of product selectivity values, obtained in experiments performing the reductive amination of glycolaldehyde (i) in the presence of Raney nickel alone, and (ii) in the presence of both Raney nickel and various zeolites as solid acid co-catalysts.

A number of experiments were conducted to investigate the performance of various zeolites, as solid (heterogeneous) acid co-catalysts with a Raney nickel catalyst, for the reductive amination of glycolaldehyde. In each case, a feed comprising 5% glycolaldehyde dimer by weight in 28% aqueous ammonia solution was reacted, together with a fixed amount of Raney nickel and the zeolite, in a high throughput screening batch reactor. A reference experiment was also performed with Raney nickel catalyst alone (in the absence of a zeolite). Another experiment as performed with Raney nickel and ammonium acetate as a homogeneous co-catalyst. The catalytic, reductive amination reactions were carried out in sealed reactors at 85 degrees Celsius (185° F.) and under 8.27 MPa (1200 psi) hydrogen pressure for a 2 hour hold period. The reaction product, following the separation from solid catalyst(s), was analyzed by GC. The results demonstrated that selectivity for monoethanolamine could be enhanced using zeolites, as solid (heterogeneous) acid co-catalysts, compared to the use of Raney nickel alone. The results including the selectivities to monoethanolamine, as well as selectivities to the byproducts ethylene glycol, ethylene diamine, and diethanolamine, are shown in FIG. 3.

The invention claimed is:

1. A process for producing taurine, comprising:
   pyrolyzing a sugar or mixture of sugars to produce a pyrolysis product mixture including glycolaldehyde and formaldehyde;
   carrying out an oxidation on the pyrolysis product mixture in the presence of a catalyst, to remove formaldehyde from the pyrolysis product mixture while retaining glycolaldehyde therein;
   combining the reduced formaldehyde pyrolysis product mixture with an aminating agent in the presence of hydrogen and a catalyst to produce a monoethanolamine product from glycolaldehyde in the reduced formaldehyde pyrolysis product mixture;
   sulfating at least a portion of the monoethanolamine product to produce 2-aminoethyl hydrogen sulfate ester; and
   sulfonating the 2-aminoethyl hydrogen sulfate ester to produce taurine.

2. The process of claim 1, wherein the glycolaldehyde is reacted with the aminating agent in the presence of both a hydrogenation catalyst and an acid co-catalyst under reductive amination conditions, to produce the monoethanolamine product.

3. The process of claim 2, wherein the conversion of glycolaldehyde to produce a monoethanolamine product takes place in an aqueous reaction mixture, to which the aminating agent is added.

4. The process of claim 3, wherein the acid co-catalyst is a solid in the aqueous reaction mixture.

5. The process of claim 4, wherein the acid co-catalyst has a density of Lewis acid sites from 200 to 1200 μmol/g.

6. The process of claim 5, wherein the acid co-catalyst comprises a zeolitic or non-zeolitic molecular sieve, a metal sieve, a metal oxide, an activated carbon, or a resin.

7. The process of claim 6, wherein the acid co-catalyst is a zeolitic molecular sieve having a silica to alumina molar framework ratio of less than 200.

8. The process of claim 6 or claim 7, wherein the acid co-catalyst is a zeolitic molecular sieve having a structure type selected from the group consisting of FAU, FER, MEL, MTW, MWW, MOR, BEA, LTL, MFI, LTA, EMT, ERI, MAZ, MEI, and TON.

9. The process of claim 8, wherein the structure type is BEA or MFI.

10. The process of claim 3, wherein the acid co-catalyst is solubilized in the aqueous reaction mixture.

11. The process of claim 10, wherein the acid co-catalyst is a metal triflate.

12. The process of claim 1, wherein the catalyst for the oxidation step is a catalyst comprising platinum and bismuth.

13. A process for producing taurine, comprising:
    pyrolyzing a sugar or mixture of sugars to produce a pyrolysis product mixture including glycolaldehyde and formaldehyde;
    contacting the pyrolysis product mixture with a sufficient quantity of a formaldehyde-scrubbing material selected from the group consisting of macroporous polystyrenic weak base anion exchange resins with primary or tertiary amine functional groups and greensand to scrub formaldehyde from the pyrolysis product mixture while leaving glycolaldehyde in the mixture;
    combining the resultant reduced formaldehyde pyrolysis product mixture with an aminating agent in the presence of hydrogen and a catalyst to produce a monoethanolamine product from glycolaldehyde in the reduced formaldehyde pyrolysis product mixture;
    sulfating the monoethanolamine product to produce 2-aminoethyl hydrogen sulfate ester; and
    sulfonating the 2-aminoethyl hydrogen sulfate ester to produce taurine.

14. A process for producing taurine, comprising:
    pyrolyzing a sugar or mixture of sugars to produce a crude pyrolysis product mixture including glycolaldehyde and formaldehyde;
    combining the crude pyrolysis product mixture without substantially removing any of the formaldehyde therefrom with an aminating agent in the presence of hydrogen and a catalytic combination including from 1 to 99 percent by total weight of a nickel catalyst component and the remainder of an acidic co-catalyst component to produce a monoethanolamine product from the crude pyrolysis product mixture;
    sulfating at least a portion of the monoethanolamine product to produce 2-aminoethyl hydrogen sulfate ester; and
    sulfonating the 2-aminoethyl hydrogen sulfate ester to produce taurine.

\* \* \* \* \*